United States Patent [19]

Wejnar

[11] Patent Number: 5,078,704

[45] Date of Patent: Jan. 7, 1992

[54] SUCTION BOTTLE FOR REDON WOUND DRAINAGE

[75] Inventor: Siegfried Wejnar, Lüneburg, Fed. Rep. of Germany

[73] Assignee: Sterimed Gesellschaft für Medizinischen Bedarf mbH

[21] Appl. No.: 110,544

[22] Filed: Oct. 16, 1987

Related U.S. Application Data

[63] Continuation of Ser. No. 865,202, filed as PCT/EP85/00427, Aug. 20, 1985, abandoned.

[30] Foreign Application Priority Data

Aug. 29, 1984 [CH] Switzerland ............... 04138/84

[51] Int. Cl.⁵ ............................................. A61M 1/00
[52] U.S. Cl. ..................................... 604/317; 604/321; 128/760; 141/236; 222/485
[58] Field of Search ............................. 604/317–321; 128/760, 762–764, 766; 222/288, 485; 141/9, 234, 236, 237, 244; 285/155

[56] References Cited

U.S. PATENT DOCUMENTS

| | | | |
|---|---|---|---|
| 1,099,713 | 6/1914 | Morris | 285/155 |
| 3,604,410 | 9/1971 | Whitacre | 128/762 |
| 3,730,170 | 5/1973 | Michael | 128/762 |
| 3,843,016 | 10/1974 | Bornhorst | 220/306 |
| 3,929,133 | 12/1975 | Ragab | 604/319 |
| 4,018,224 | 4/1977 | Kurtz et al. | 604/321 |
| 4,376,439 | 3/1983 | Lauterjung | 604/318 |
| 4,445,884 | 5/1984 | Kurtz et al. | 604/317 |

FOREIGN PATENT DOCUMENTS

| | | | |
|---|---|---|---|
| 0008450 | 3/1980 | European Pat. Off. | |
| 0036546 | 9/1981 | European Pat. Off. | |
| 0082510 | 6/1983 | European Pat. Off. | 604/319 |
| 2249119 | 10/1972 | Fed. Rep. of Germany | 128/762 |
| 2934915 | 3/1981 | Fed. Rep. of Germany | 604/319 |
| WO80/02706 | 12/1980 | PCT Int'l Appl. | 604/317 |

Primary Examiner—Randy Citrin Shay
Attorney, Agent, or Firm—Toren, McGeady & Associates

[57] ABSTRACT

An evacuated suction bottle 1 for wound drainage, which comprises two chambers 2, 3 separated from one another, is described.

7 Claims, 3 Drawing Sheets

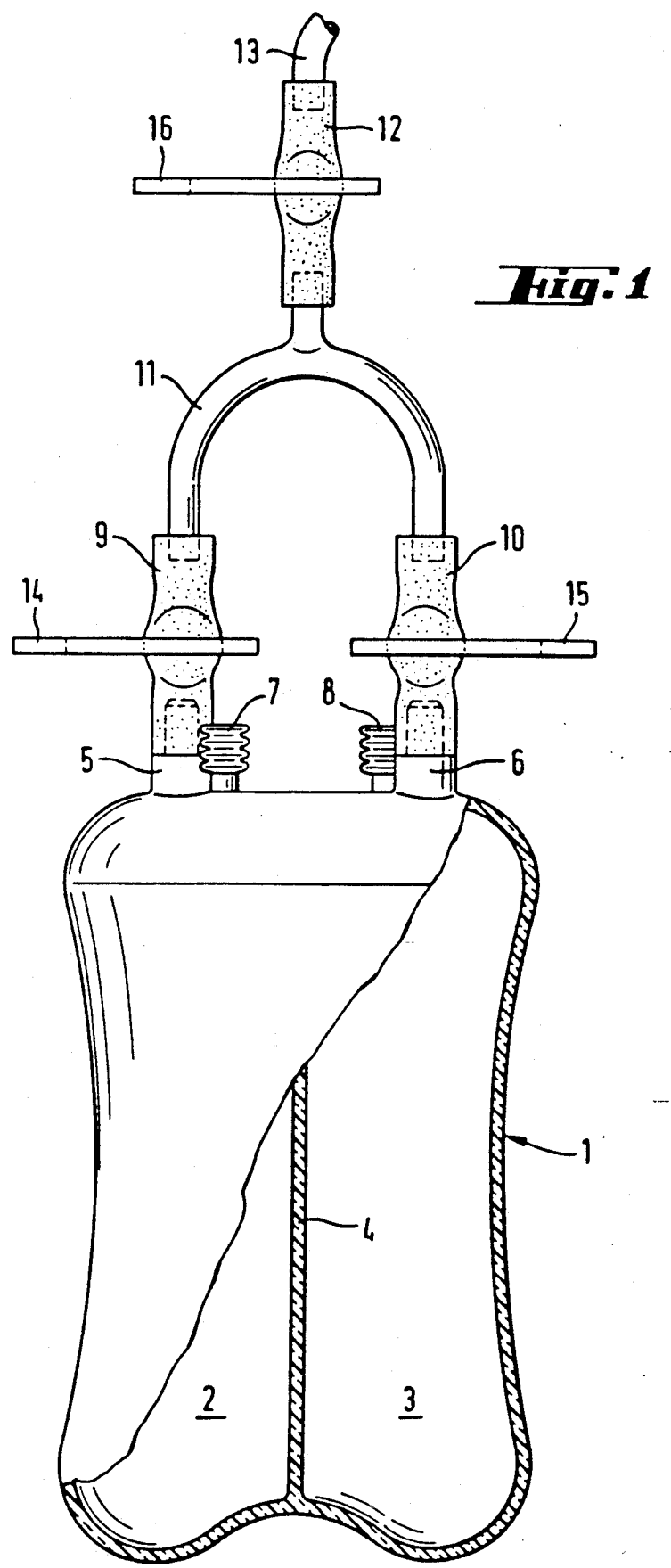

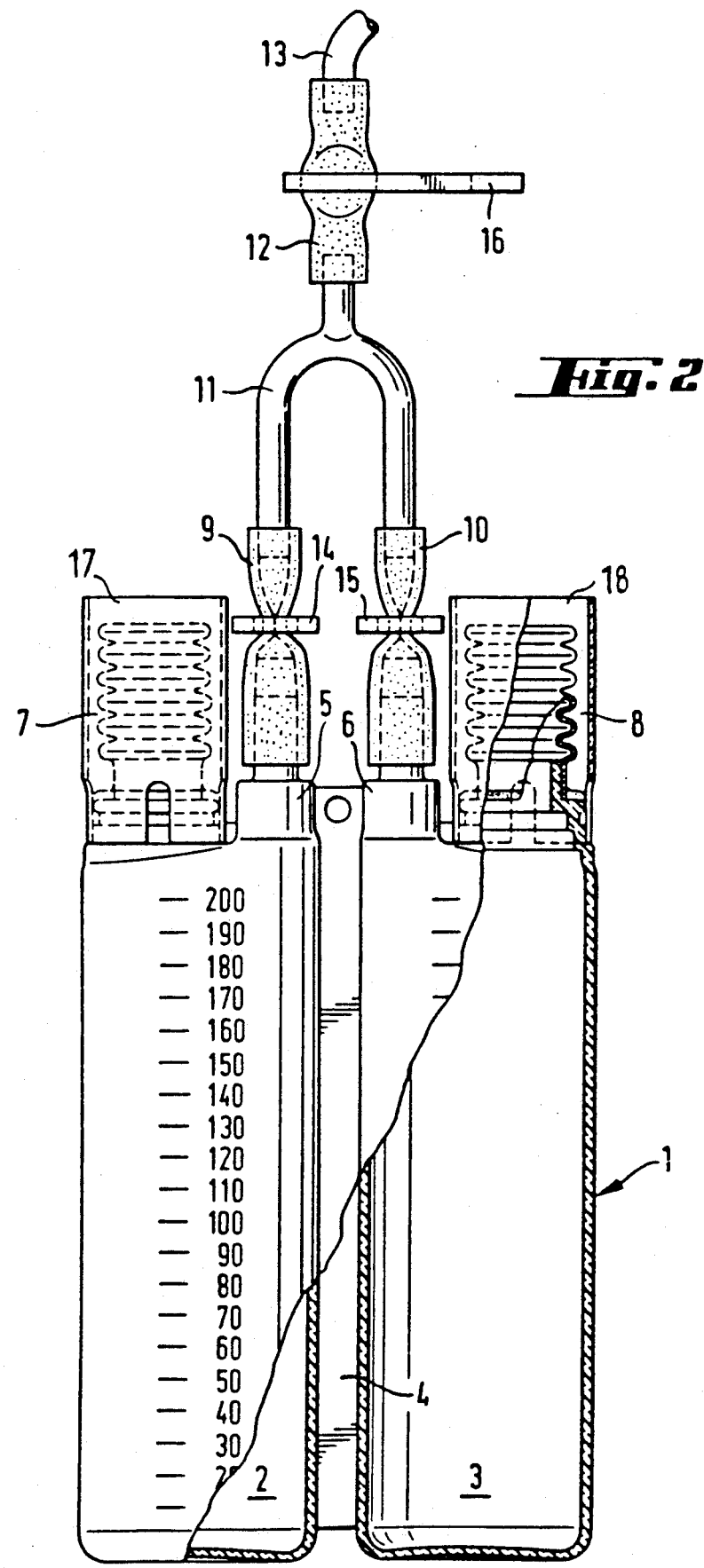

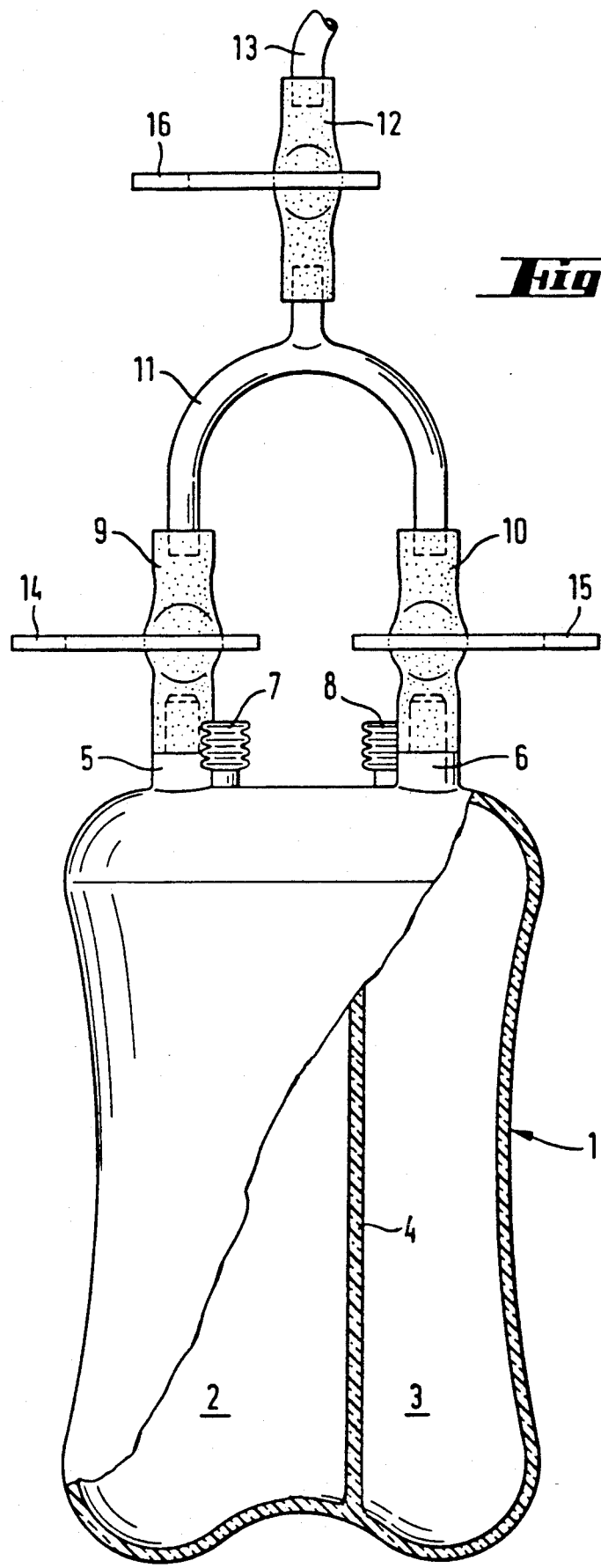

SUCTION BOTTLE FOR REDON WOUND DRAINAGE

This is a continuation of Ser. No. 865,202, filed April 25, 1986 now abandoned.

TECHNICAL FIELD

The invention relates to an evacuated suction bottle for wound drainage.

STATE OF THE ART

Post-operative wound drainage by means of a large reduction in pressure (sometimes referred to as the Redon technique) is now in very frequent use. German Auslegeschrift 2,639,715 describes a one-piece disposable bottle made of plastic, with a pressure indicator and a connector for a tube leading to a wound drain. These bottles are subjected, under sterile conditions, to a reduction in pressure of more than 90 kPa. Consequently, when they are attached to a wound drain, a corresponding pressure difference arises between the wound cavity, in which the drain is located, and the environment. As a result of this pressure difference, the wound surfaces are pressed against one another, thus immobilizing the wound gap. It thereby becomes easier for the tissue to bridge the wound gap, that is to say the healing of the wound is assisted.

A closed system is used for wound drainage according to the Redon technique. Contamination via the drainage system is therefore largely prevented. A problem arises, however, when the system is opened, this being necessary, for example, when the suction bottle is changed. It is particularly dangerous to change a bottle when, inadvertently, the suction line has not been sealed off beforehand. In this case, discharge and bacteria-laden ambient air are sucked into the wound. Moreover, the pressure difference between the environment and the interior of the wound is compensated, and the undesirable result of this is that the edges of the wound cease to be pressed together. Bacteriological tests (A. Harle, Hygiene and Medicine 7 [1982]427) show that, in particular, the bottle change has an adverse effect on the sterility conditions of the wound drainage system. The bottle change can also be harmful to the nursing staff, since there is a danger of contact with possibly infectious wound discharge.

In some uses, it is expedient to exert less suction at the start of wound drainage. This can be achieved by first using a partially ventilated suction bottle which is then exchanged later for a suction bottle with a full vacuum. With this too, problems as regards sterility can arise when a bottle is changed.

DESCRIPTION OF THE INVENTION

The object of the invention was to provide an evacuated suction bottle for Redon wound drainage, by means of which the dangers associated with the bottle change can be avoided.

According to the invention, this object is achieved because the suction bottle comprises two chambers separated from one another. The two chambers of the suction bottles which are the subject of the invention either have an essentially identical inner volume or are characterized by different inner volumes.

A preferred subject is suction bottles whose two chambers are each equipped with a pressure indicator. The chambers are connected to one another and to a connecting tube via a Y-piece, and all the inlets of the Y-piece can be pinched off.

In the state as delivered, the two chambers of the suction bottle according to the invention are evacuated and all the connectors of the Y-piece are pinched off by means of clamps. When the suction bottle is used, the free connector of the Y-piece is connected to the connecting tube leading to the wound drain. The clamps on the originally free connector of the Y-piece and the clamp between the Y-piece and the first chamber of the suction bottle are then opened. At the time when a bottle would be changed if conventional single-chamber suction bottles were used, the clamp between the Y-piece and the first chamber is closed and the clamp between the Y-piece and the second chamber is opened. Further wound discharge now flows into the second chamber. This "switch-over" from the first chamber to the second chamber avoids the risks associated with the bottle change.

If desired, instead of the "switch-over" described, the closure of the clamp between the Y-piece and the first chamber can be omitted, and pressure compensation between the two chambers can be obtained by opening the clamp between the Y-piece and the second chamber. In this case, the remaining volume of the first chamber is also available for further drainage.

A further alternative in the use of the double-chamber suction bottle according to the invention is to reduce the vacuum in the first chamber to a desired value before a conducting connection is made between the first chamber and the wound drain, that is to say before the clamp between the Y-piece and the first chamber is opened. This can be carried out, for example, by piercing with a thin puncture cannula the concertina used as a pressure indicator or another rubber part acting as a self-sealing diaphragm. To prevent bacteria from being drawn in from the ambient air, the cannula is provided with a bacteria filter at its rear end. By means of this pressure reduction, wound drainage can be started with less suction and later can be continued with increased suction as a result of a "switch-over" to the second chamber or "switch in" of the second chamber. This procedure is considered advantageous in certain surgical operations and, when the double-chamber bottle according to the invention is used, can take place without a bottle change.

The suction bottle according to the invention is produced by processes known per se. For example, the bottle is made by joining together two half-bottles, for example by glueing or welding. The half-bottles can be produced in the usual way by blow molding.

The volume of the suction bottle can be varied within wide limits, depending on the intended use. For example, for draining small wounds, such as occur, for example, in hand-surgery operations, a suction bottle with a total volume of 100 to 200 $cm^3$ can be provided. For larger operations, the suction bottles can have a total volume of, for example, 800 to 1000 $cm^3$. Suction bottles with a total volume of 400 to 600 $cm^3$ are preferred.

Suction bottles in which the two chambers have different volumes can be produced for special purposes.

In one embodiment of the invention, the suction bottle consists of two separate bottles which each have a pressure indicator and a connector for a tubing line and are connected firmly to one another by means of a common mounting and the interiors of which are connected to one another and to a connecting line via a Y-piece.

The pressure indicator used can, for example, be one of those which are customary in the conventional evacuated suction bottles for wound drainage. Further relevant embodiments of pressure indicators for suction bottles are described, for example, in EP-A2-0,061,723 and EP-A2-0,036,546.

The invention is explained in detail below with reference to two exemplary embodiments. FIG. 1 shows a suction bottle in a partially diagrammatic representation. FIG. 1a shows a suction bottle with chambers of different size. FIG. 2 shows a further embodiment.

The suction bottle 1 in FIG. 1 is shown partially cut away. A partition wall 4 separates the interior of the suction bottle 1 into a first chamber 2 and a second chamber 3. The suction bottle 1 has, for each of the chambers 2, 3, a connector 5, 6 and a pressure indicator 7, 8. In the exemplary embodiment shown in FIG. 1, the pressure indicators 7, 8 are represented as concertinas. Drawn onto the connectors 5, 6 are tube connection pieces 9, 10 which make the connection to the Y-piece 11. Attached on the remaining outlet of the Y-piece 11 is a tube connection piece 12 which makes the connection to the connecting tube 13 leading to the wound drain (not shown). Sliding clamps 14, 15, 16 are attached on the tube connection pieces 9, 10, 12.

FIG. 2 illustrates a further embodiment of a suction bottle 1 in a partially cut away representation. Here, the partition wall 4 is designed as a connecting web between the two chambers 2 and 3 of essentially cylindrical cross-section. Scales, by means of which the particular filling level of the chambers can be read off, are marked on the outsides of the chambers 2 and 3. As in the embodiment according to FIG. 1, the pressure indicators 7 and 8 are designed as concertinas surrounded by sleeves 17 and 18, on which scales for indicating the pressure in the chambers 2 and 3 can be marked. The remaining elements which have been given reference symbols correspond to those in FIG. 1.

I claim:

1. Evacuated suction bottle for wound drainage, wherein the suction bottle (1) comprises two chambers (2, 3) separated from one another, a Y-piece for connecting the chambers (2, 3) to one another and to a connecting tube (13), and three means for individually pinching off each of the three inlets of the Y-piece (11).

2. Suction bottle as claimed in claim 1, wherein the two chambers (2, 3) have an essentially identical inner volume.

3. Suction bottle as claimed in claim 1, wherein the two chambers (2, 3) have different inner volumes.

4. Suction bottle as claimed in claim 1, wherein the chambers (2, 3) together have an inner volume of 100 to 1000, $cm^3$.

5. Suction bottle as claimed in claim 4, wherein the chambers together have an inner volume of 400 to 600 $cm^3$.

6. Suction bottle as claimed in claim 1, wherein the chambers (2, 3) are each designed separately as independent suction bottles which are connected firmly to one another by means of a common mounting.

7. Suction bottle as claimed in claim 1, wherein the chambers (2, 3) each have a pressure indicator (7, 8).

* * * * *